US006210334B1

(12) United States Patent
Phillips

(10) Patent No.: US 6,210,334 B1
(45) Date of Patent: Apr. 3, 2001

(54) MEDICAL DIAGNOSTIC ULTRASOUND METHOD AND APPARATUS FOR HARMONIC DETECTION USING DOPPLER PROCESSING

(75) Inventor: Patrick J. Phillips, Sunnyvale, CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/282,902

(22) Filed: Mar. 31, 1999

(51) Int. Cl.[7] ........................................................ A61B 8/06

(52) U.S. Cl. .............................................................. 600/453

(58) Field of Search ..................................... 600/437, 443, 600/447, 453, 455, 458, 457; 367/7, 11, 138; 73/625

(56) References Cited

U.S. PATENT DOCUMENTS

| | | | |
|---|---|---|---|
| 3,953,823 | * | 4/1976 | Katakura .............................. 340/1 R |
| 5,083,567 | * | 1/1992 | Uchibori .............................. 600/455 |
| 5,170,792 | | 12/1992 | Sturgill et al. . |
| 5,197,477 | | 3/1993 | Peterson et al. . |
| 5,327,894 | | 7/1994 | Thomas . |
| 5,349,524 | | 9/1994 | Daft et al. . |
| 5,349,525 | | 9/1994 | Dunki-Jacobs et al. . |
| 5,357,965 | | 10/1994 | Hall et al. . |
| 5,431,169 | * | 7/1995 | Gondo ................................. 600/455 |
| 5,445,156 | | 8/1995 | Daft et al. . |
| 5,456,257 | | 10/1995 | Johnson et al. . |
| 5,487,389 | | 1/1996 | Banjanin et al. . |
| 5,494,037 | | 2/1996 | Banjanin et al. . |
| 5,524,629 | | 6/1996 | Mahony . |
| 5,544,659 | | 8/1996 | Banjanin . |
| 5,664,575 | | 9/1997 | Banjanin et al. . |
| 5,706,819 | | 1/1998 | Hwang et al. . |
| 5,782,769 | * | 7/1998 | Hwang et al. ....................... 600/454 |
| 5,833,613 | | 11/1998 | Averkiou et al. . |
| 5,882,315 | * | 3/1999 | Ji et al. ............................... 600/553 |
| 5,910,118 | * | 6/1999 | Kanda et al. ........................ 600/455 |
| 5,951,478 | * | 9/1999 | Hwang et al. ...................... 600/443 |
| 5,993,391 | * | 11/1999 | Kamiyama ......................... 600/443 |
| 6,048,316 | * | 4/2000 | Zhao et al. .......................... 600/447 |

OTHER PUBLICATIONS

David Hope Simpson and Peter N. Burns, "Pulse Inversion Doppler: A New Method for Detecting Nonlinear Echoes from Microbubble Contrast Agents", 1997 IEEE International Ultrasonics Symposium, Toronto, Canada, Oct. 5–8, 1997, pp. 1597–1600.

Simpson et al., "Perfusion Imaging with Pulse Inversion Doppler and Microbubble Contrast Agents: In Vivo Studies of the Myocardium", 1998 IEEE International Ultrasonics Symposium, Sendai, Miyagi, Japan, Oct. 5–8, 1998; A–3.

Simpson et al. "Pulse Inversion Doppler: A New Method for Detecting Nonlinear Echoes from Microbubble Contrast Agents", submitted to IEEE Trans. Ultrason., Ferroelectrics., Freq. Cntrol.

Shariati, M.A., Dripps, J.H., and McDicken, W.N., "Deadbeat IIR Based MTI Filtering for Color Flow Imaging Systems".

(List continued on next page.)

Primary Examiner—Marvin M. Lateef
Assistant Examiner—Ali M. Imam
(74) Attorney, Agent, or Firm—Craig A. Summerfield, Esq.; Brinks Hofer Gilson & Lione

(57) ABSTRACT

A method and system for detecting energy using pulse inversion and Doppler processing are provided. Pulse inversion may be used to image the harmonic response of tissue alone or with contrast agents. Lowpass or bandpass clutter filters suppress the harmonic and/or fundamental response of tissue clutter to provide improvements in imaging, such as for imaging small vessels. Elimination of tissue clutter from both the fundamental components and second harmonic components in the Doppler domain increases the specificity of contrast agent and/or tissue.

125 Claims, 6 Drawing Sheets-

OTHER PUBLICATIONS

Kadi, A.P., and Loupas, T., "On the Performance of Regression and Step–Initialized IIR Clutter Filters for Colour Doppler Systems in Diagnostic Medical Ultrasound", IEEE Trans. Ultrason., Ferroelectrics., Freq. Cntrol.

Peterson, R.B., Atlas, L.E., and Beach, K.W., "A Comparison of IIR Initialization Techniques for Improved Color Doppler Wall Filter Performance", IEEE Ultrasonics Symposium, pp. 1705–1708, 1994.

Bjaerum, S. et al., Optimal Adaptive Clutter Filtering In Color Flow Imaging; 1997 IEEE Ultrasonics Symposium, pp. 1223–1226.

Chornoboy, S., "Initialization for Improved IIR Filter Performance", IEEE Trans. On Signal Processing, vol. 40, No. 3, pp. 543–550, 1992.

* cited by examiner

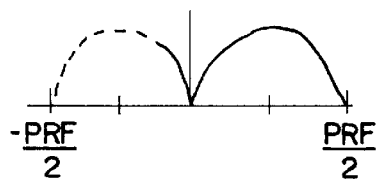
FIG. 4A
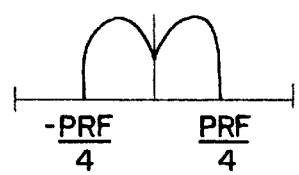
FIG. 4B
FIG. 5
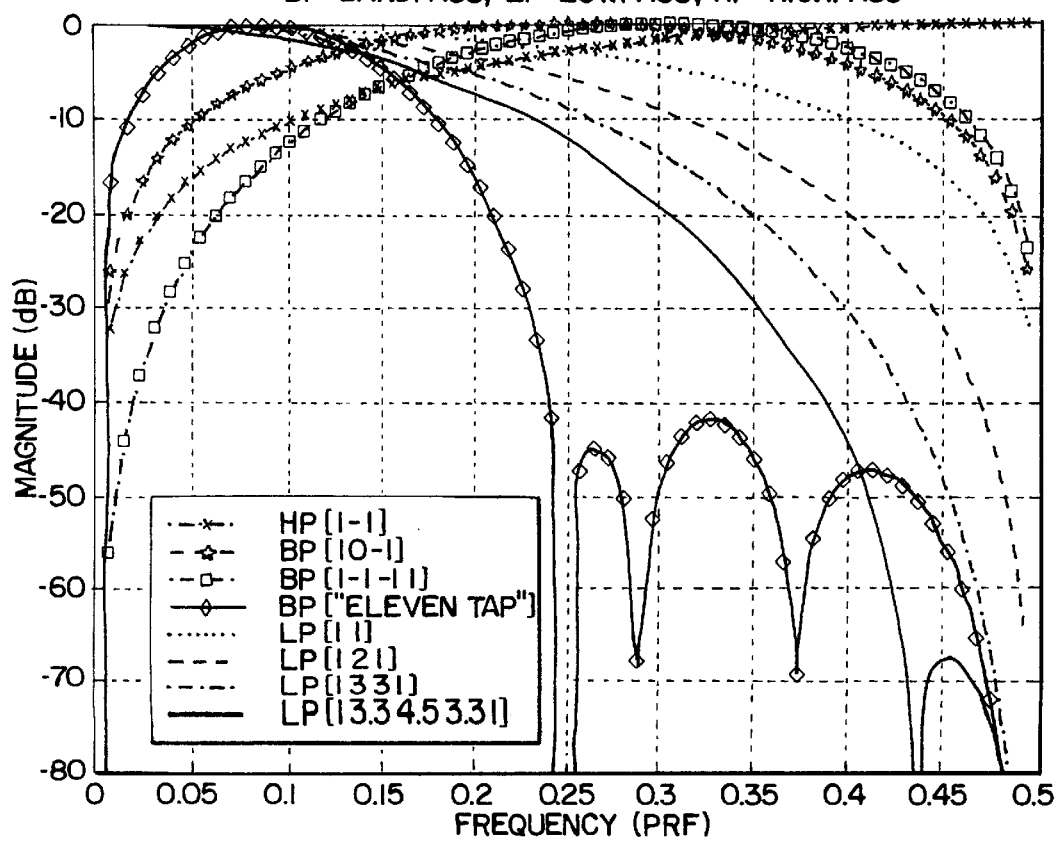

MEDICAL DIAGNOSTIC ULTRASOUND METHOD AND APPARATUS FOR HARMONIC DETECTION USING DOPPLER PROCESSING

BACKGROUND OF THE INVENTION

This invention relates to medical diagnostic ultrasound systems and methods for detecting harmonic energy using Doppler processing. In particular, pulse inversion techniques are used with Doppler detection.

Imaging of small vessels may increase the potential for obtaining diagnostic information. One method for enhancing the imaging of small vasculature is the injection of contrast agents. Using B-mode imaging, the injected contrast agents may increase specificity. By isolating signals associated with a second harmonic of the fundamental transmit frequency, contrast agents may further increase the specificity for imaging small vasculature. However, many vessels, such as small vessels in the myocardium may remain undetected using these techniques.

Lost pulse-to-pulse correlation may help identify small vessels in a B-mode image of contrast agents due to visible temporal flickering, but the lost correlation can also be used in Doppler imaging to further increase contrast agent to tissue specificity. In Doppler, two or more pulses are transmitted in the same direction, and differences between the pulses are highlighted by Doppler processing. Using the Doppler frequency shift to show movement may identify moving contrast agents in small vessels. Using harmonic detection with Doppler processing (i.e. harmonic Doppler), contrast agents and vessels may be detected below the resolution limits of B-mode imaging. However, clutter associated with moving tissue may limit the resolution and detectability of small vessels.

Another technique, pulse inversion, for increasing the specificity of contrast agents for ultrasound imaging is disclosed by Hwang et al. in U.S. Pat. No. 5,706,819 (the '819 patent). Contrast agent is injected into a target. Two or more pulses are transmitted on the same scan line within the target. Each pulse is associated with a different envelope phase or polarity, such as transmitting the first pulse with the phase of zero degrees and transmitting the second pulse with a phase of 180 degrees. By adding the consecutive echo pairs associated with these transmissions, i.e., $P^1+P^2$, $P^2+P^3$, etc., the fundamental components are suppressed and the harmonic components of the echo signals are summed. If fundamental components are suppressed, shorter transmit pulses for increased axial resolution and finer spatial sampling of flow may be used.

In the Doppler domain, pulse inversion provides a spectrum with separated odd and even harmonics. Odd harmonic components, including the dominant fundamental response, are modulated by half the pulse repetition frequency, and echoes from the even harmonics remain unmodulated at the zero frequency. Provided that a velocity scale is chosen to minimize aliasing, such as using half the conventional limit, odd and even harmonics can be uniquely identified in the Doppler domain.

Pulse inversion Doppler techniques may increase the specificity of contrast agents, allowing for better imaging of small vessels. The ratio of non-linear response to linear response using Doppler energy may identify contrast agent with improved specificity. This contrast improvement may allow for transmissions at reduced power, providing less contrast agent destruction and possibly larger durations of agent enhancement.

In the above-discussed '819 patent, the non-linearity associated with the tissue is assumed to be negligible (column 5, line 15). However, the non-linear response from tissue can be significant. These non-linearities can introduce unwanted harmonic clutter that interferes with detection of non-clutter harmonic energy. Two pulse summation or multiple pulse summation by "accumulating the partial sum of consecutive pairs of echoes" (column 6, line 4) is disclosed. This two echo pair summation of sequentially acquired ultrasound lines provides a lowpass Doppler wall, or clutter, filter with an impulse response of [1 1]. Two echo summation limits the ability of the disclosed system to optimally suppress fundamental clutter. Pulse to pulse pair summations may suppress some fundamental clutter at, or near, plus or minus one half the PRF, but may not suppress harmonic clutter near DC. Further, the [1,1] impulse response can be ineffective for even slight movements of clutter signal sources, introducing deleterious clutter and masking the signals of interest.

In "Pulse Inversion Doppler: A New Method for Detecting Nonlinear Echoes from Microbubble Contrast Agents", 1997 IEEE International Ultrasonics Symposium, Toronto, Canada, Oct. 5–8, 1997, by D. Simpson et. al., the use of a modified wall filter is noted. Using the modified wall filter for pulse inversion with Doppler imaging provides 15 dB more agent to tissue contrast in the myocardium than for harmonic Doppler processing. In "Perfusion Imaging with Pulse Inversion Doppler and Microbubble contrast Agents: In Vivo Studies of the Myocardium", 1998 IEEE International Ultrasonics Symposium, Sendai, Miyagi, Japan, Oct. 5–8, 1998, D. Simpson et. al., suggest that such wall filters can be designed and a specific type of filter design taken from MTI Doppler RADAR theory is used for estimating energy only, not velocities or variances, before and after contrast injections. However, further modifications of the wall filters are not discussed, and the desired filtering of harmonic and fundamental clutter signals may be further optimized.

BRIEF SUMMARY

The present invention is defined by the following claims, and nothing in this section should be taken as a limitation on those claims. By way of introduction, the preferred embodiment described below includes a method and system for harmonic detection using pulse inversion and Doppler processing. Pulse inversion may be used to image the harmonic response of tissue alone or with contrast agents. Lowpass or bandpass clutter filters suppress the harmonic and/or fundamental response of tissue clutter to provide improvements in imaging, such as for imaging small vessels. Elimination of tissue clutter from both the fundamental components and second harmonic components increases the specificity of contrast agent and/or tissue without the use of contrast agents.

In one preferred embodiment, signals including harmonic energy are detected with a medical diagnostic ultrasound system. A first pulse is transmitted with a first polarity from a transducer, and a second pulse is transmitted with a second polarity. Receive signals responsive to the two transmissions are filtered with a lowpass filter. Doppler processing is then applied to the filtered receive signals. In further embodiments, a bandpass filter may be used for clutter filtering.

In another embodiment discussed below, signals including harmonic energy are detected from a target with a medical diagnostic ultrasound system. A first ultrasonic pulse is transmitted with a first polarity into a target along a scan line during an imaging session where the target is free of contrast agent throughout the entire imaging session. A second ultrasonic pulse of a second polarity is also transmitted into the target along the scan line during the imaging session. Receive signals responsive to the transmissions that are associated with the same depths along the scan line are filtered and Doppler processed.

Further aspects and advantages are discussed below in conjunction with the preferred embodiments.

BRIEF DESCRIPTION OF SEVERAL VIEWS OF THE DRAWINGS

FIGS. 4A and 4B are graphical representations of frequency responses of bandpass clutter filters.

FIG. 5 is a graphical representation of various filter responses.

DETAILED DESCRIPTION OF THE PREFERRED EMBODIMENT

Figure 1:
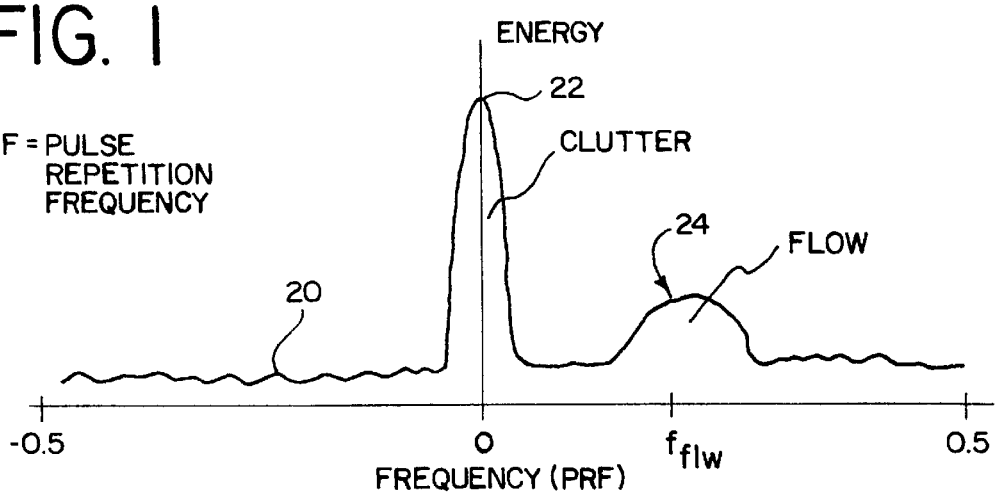
FIG. 1 is a graphical representation of a Doppler spectrum.

Small vessels, other tissue, including blood, and optionally contrast agent are imaged using pulse inversion with Doppler techniques. Pulse inversion provides separated odd and even harmonic information in the Doppler frequency domain, allowing for optimal clutter filtering. Referring to FIG. 1, a Doppler spectrum 20 associated with the transmission at a fundamental frequency band of a plurality of transmit pulses with a same phase is shown. Neglecting the temporal windowing effects on a limited number of pulses, the Doppler spectrum 20 includes energy 22 responsive to tissue or clutter and energy 24 responsive to flow. The clutter energy 22 is at or near the zero Doppler frequency, and the flow energy 24 is at a frequency $f_{flw}$. The value of the mean Doppler frequency of the flow energy and associated mean velocity are determined as a function of the pulse repetition frequency.

Figure 2:
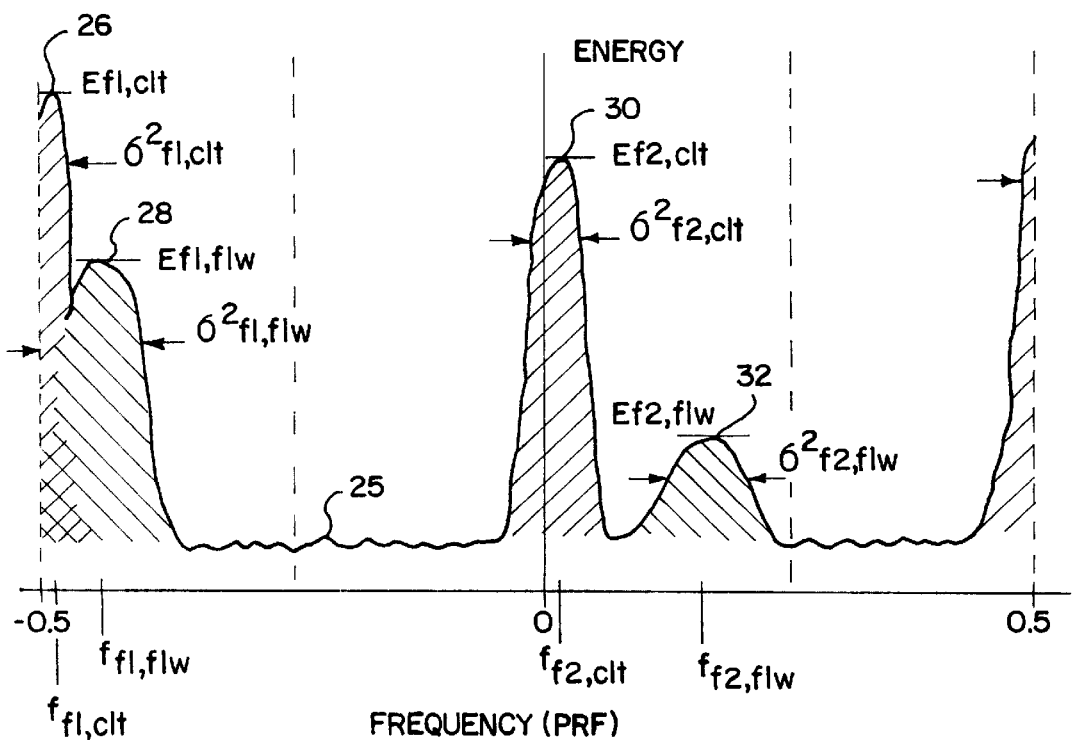
FIG. 2 is a graphical representation of a Doppler spectrum associated with pulse inversion.

By using phase inversion, the fundamental and even harmonic spectra are separated as shown in FIG. 2. The spectrum 25 includes energy 26 responsive to clutter at odd harmonics, including the fundamental frequency, energy 28 responsive to flow at the odd harmonics, including the fundamental frequency, energy 30 responsive to clutter at even harmonic frequencies, and energy 32 responsive to flow at even harmonic frequencies. Each of these responses is defined in terms of a peak energy, a frequency associated with the peak energy and a variance, where: $f_{f1,clt}$ and $f_{f2,clt}$ represent the mean frequency of clutter signals at the fundamental and even harmonic frequencies, respectively, $f_{f1, flw}$ and $f_{f2, flw}$ represent the mean frequency of flow signals at the fundamental and even harmonic frequencies, respectively, $\sigma_{f1, clt}$ and $\sigma_{f2, clt}$ represent the variance and proportional bandwidth of the clutter at the fundamental and even harmonic frequencies, respectively, $\sigma_{f1, flw}$ and $\sigma_{f2, flw}$ represent the variance and proportional bandwidth of the flow at the fundamental and even harmonic frequencies, respectively, $E_{f1, clt}$ and $E_{f2, clt}$ represent the energy of the clutter signals at the fundamental and even harmonic frequencies, respectively, and $E_{f1, flw}$ and $E_{f2, flw}$ represent the energy of flow signals at the fundamental and even harmonic frequencies, respectively. f1 indicates components due to the fundamental and possibly some odd harmonics. f2 indicates components due to even harmonics, such as the second harmonic.

By providing appropriate filtering, the clutter energy 26, 30 of the fundamental and/or harmonic components may be reduced. For example, a bandpass filter reducing energy associated with ½ and −½ the pulse repetition frequency (PRF) and at the zero frequency reduces clutter of the fundamental and harmonic components. A lowpass filter may be used to remove the clutter energy 26 of the fundamental component. These filtering schemes maintain the flow signals of interest for subsequent parameter estimation and display processing.

Figure 3:
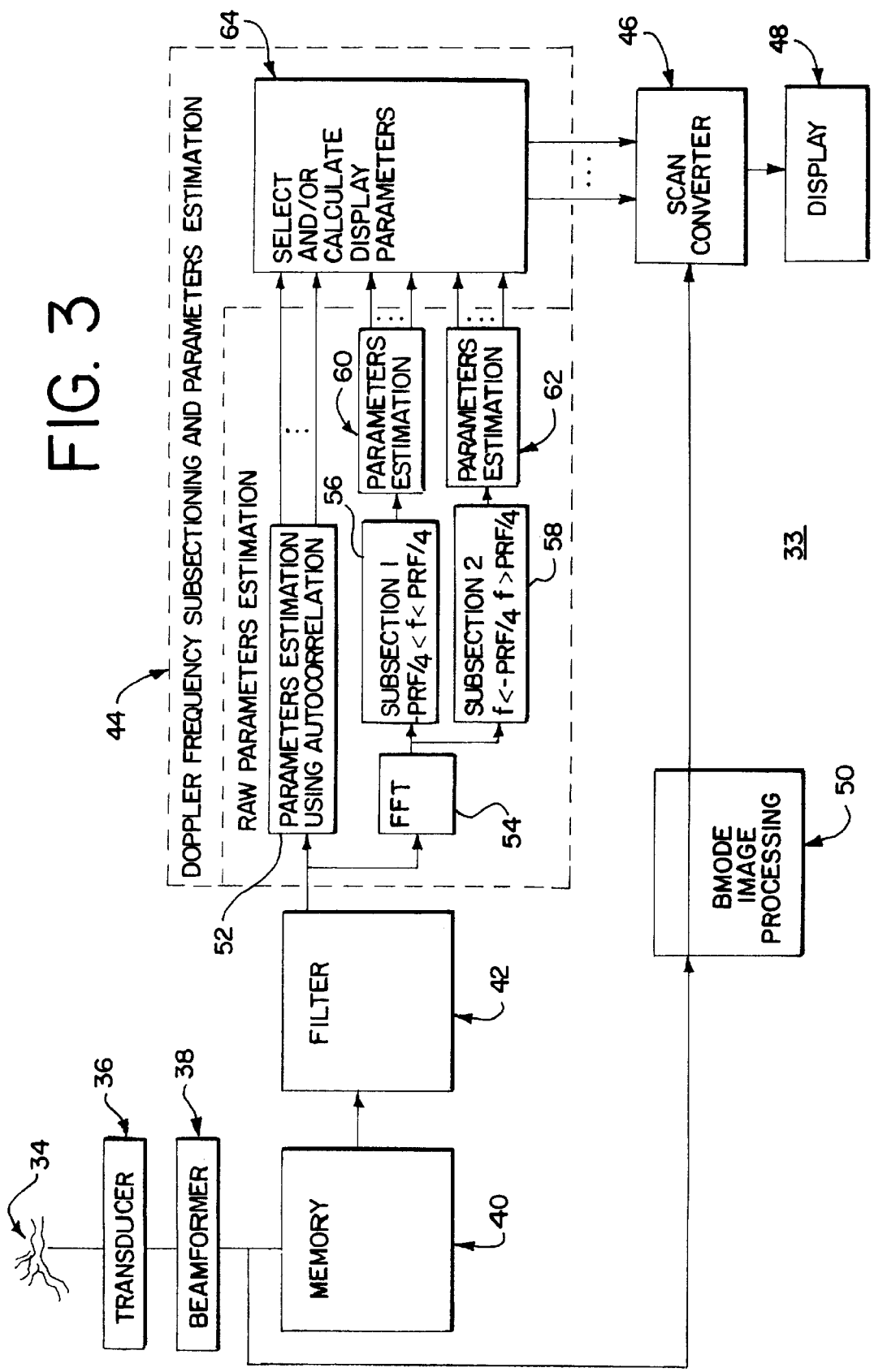
FIG. 3 is a block diagram of one embodiment of a medical diagnostic ultrasound system for Doppler detection.

Referring to FIG. 3, a block diagram of one preferred embodiment of a medical diagnostic ultrasound system for Doppler detection using pulse inversion is shown at 33. The system 33 includes a transducer 36, a beamformer 38, a memory 40, a filter 42, a Doppler processor 44, a scan converter 46, and a display 48. Optionally, a B-mode processor 50 or other imaging processor may be included. The B-mode processor provides conventional B-mode processing from coherently summed information for generating an image on the display 48.

The transducer 36 comprises a linear or a multiple dimension array. The beamformer 38 operates, in part, as a conventional transmit beamformer to generate a set of transmit signals for individual transducer elements included in the transducer 36. For example, the beamformer 38 may include a waveform generator that applies a suitably shaped transmit signal. The ultrasonic pulse comprises the set of transmit signals and is associated with a frequency band. The frequency band of the ultrasonic pulse comprises a fundamental transmit frequency band. A frequency band includes a center frequency. As used herein, the fundamental or harmonic frequency comprises the center of the fundamental or harmonic frequency band.

The transmit signals are delayed for focusing the ultrasonic pulse. The focus delay provides conventional steering delays by any suitable combination of delays, phase shifts and phase rotations. The focus delays are selected to cause the ultrasonic signals from the transducer array 36 to constructively interfere at a selected transmit focus along a selected transmit beam or scan line direction.

In one embodiment, the envelope phase associated with every other ultrasonic pulse along a scan line is inverted. In this embodiment, a first ultrasonic pulse is transmitted with a positive polarity, such as zero degrees. A second ultrasonic pulse is inverted to provide a negative polarity, such as 180 degrees. Different polarities may be provided for two or more pulses. For example, a series of three or more ultrasonic pulses are transmitted with each pulse corresponding to a different polarity, such as zero degrees, 90 degrees and 180 degrees, respectively. Various combination of ultrasonic pulses transmitted with different polarities may be transmitted along the same scan line.

The transducer 36 transmits the ultrasonic pulse into a target 34. The target may optionally include contrast agents. Echo signals from tissue, which may include blood, or contrast agents within the target 34 are reflected back to the transducer 36.

Electric signals generated by the transducer 36 in response to the echo signals are processed by the beamformer 38. The beamformer 38 acts as a conventional receive beamformer to generate a plurality of receive signals associated with various depths along one or more scan lines. The signals are generated by applying appropriate delays and phase rotations to coherently sum the electric signals from the various transducer elements of the transducer array 36. The coherently summed signals are associated with echo signals at the fundamental and harmonics of the fundamental transmit frequency. In alternative embodiments, filtering may be provided to isolate information at either the fundamental frequency, a harmonic frequency, or some combination thereof.

The coherently summed signals are provided to the memory 40. The memory 40 comprises a corner turning memory or other memory device for storing receive signals associated with two or more transmissions of ultrasonic pulses along the same scan line. The memory 40 provides receive signals associated with the same scan line and same depth but different transmissions to the filter 42.

The filter 42 comprises a clutter filter for removing or reducing the energy associated with clutter. In one embodiment, the clutter filter 42 comprises a bandpass filter. In another embodiment the clutter filter 42 comprises a lowpass filter or a highpass filter. The filter 42 is implemented using a digital signal processor or other processor or filter device. The digital filter may provide an infinite impulse response (IIR), a finite impulse response (FIR), or adaptive techniques as discussed below. If an IIR filter is used, an initialization scheme to minimize transients is preferably provided. The implementation of the filter 42 may provide for real filtering or complex filtering.

In one preferred embodiment, the filter 42 comprises a bandpass filter. The bandpass filter may comprise separate lowpass and highpass filter stages in any order. A lowpass filter may be provided as part of a bandpass filter. Referring to FIGS. 4A and 4B, two filter responses for bandpass filtering in the Doppler domain are represented. FIG. 4A includes a stopband or null at or near one half the negative or positive pulse repetition frequency and at or near the zero frequency. This filter response attenuates clutter associated with both fundamental and harmonic components. The energy associated with flow at the harmonic and fundamental frequencies is passed or minimally attenuated. As shown in FIG. 4B, the bandpass filter response may also attenuate energy associated with flow at the fundamental frequency. Other bandpass filters and associated responses may be used to attenuate energy associated with any frequency, such as energy associated with flow at the harmonic frequency.

Referring to FIG. 5, three bandpass (BP) filters, four lowpass (LP) filters and a conventional highpass (HP) filter are shown. The highpass filter defined by coefficients [1, −1] suppresses clutter associated with the even harmonic response. The bandpass filter defined by coefficients [1, 0, −1] is also shown. An alternative bandpass filter defined by coefficients [1, −1, −1, 1] is shown and may improve the suppression of clutter at the harmonic frequency. An eleven tap filter with coefficients [1,3.9,7.5,9.2,6.5,0,−6.5,−9.2,−7.5,−3.9,−1] is shown for retaining flow signals at the harmonic frequency. Four lowpass filters with coefficients [1, 1], [1,2,1], [1,3,3,1], and [1,3.3,4.5,3.3,1] are also shown. In these examples of lowpass filters, the filters with a greater number of coefficients provide increased stop band rejection for improved fundamental clutter suppression. Filters with two or more coefficients maybe used with unequal weightings, such as [0.95, 1].

As shown in FIG. 5, the various filters comprise real filters with symmetry about the zero frequency. Complex filters and associated non-symmetric nulls within the one pulse repetition frequency range may be used.

Receive signals associated with an ultrasonic pulse transmission are provided for each of the taps or coefficients of the filter 42. For the above referenced three tap bandpass filter, three receive signals for each spatial location are provided for one output of the filter 42. For Doppler energy processing only one output signal is required, so only three sets of receive signals are provided. For the eleven tap bandpass filter, a minimum of eleven receive signals are needed to estimate Doppler energy. Additional receive signals may be used. For Doppler velocity and variance processing, two or more outputs from the filter 42 are provided. For the three tap filters discussed above, at least four receive signals are input for Doppler velocity and Doppler variance processing, such as pulses corresponding to 0, 180, 0, 180 phasing. Additional pulses provide corresponding increases in accuracy for the estimates. With IIR filter designs, fewer receive pulses may be used for similar or improved stopband, transition-band, and passband filter characteristics.

Receive signals are filtered for each spatial location within a region of the target, and the filter applied to the receive signals may vary between spatial locations. The signal or signals output from the filter 42 are provided to the Doppler processor 44. The Doppler processor 44 includes a digital signal processor, a general processor with software control, a plurality of processors or other structure for performing Doppler, FFT, or auto-correlation algorithm processing. The Doppler processor 44 generates estimates of one or more Doppler parameters, such as velocity, frequency, energy or variance for each spatial location.

In one embodiment shown in FIG. 3, the Doppler processor 44 includes two paths for estimating Doppler parameters. A first path comprises a parameter estimator 52. A second path comprises a fast Fourier transform 54, two subsections 56 and 58 and two parameter estimators 60 and 62. In alternative embodiments, only one or additional paths may be provided.

In the first path, the parameter estimator 52 uses an auto correlation algorithm to estimate Doppler parameters. In one embodiment, the filter 42 significantly attenuates energy at Doppler frequencies greater than one quarter the pulse repetition frequency and less than minus one quarter of the pulse repetition frequency, such as using the eleven tap bandpass filter discussed above. Using this filter, the parameter estimator 52 estimates the Doppler frequency, variance and energy associated with the flow at the second harmonic frequency (i.e., even harmonics). The clutter associated with the second harmonic frequency and the clutter and flow associated with the fundamental frequency are attenuated by the filter. The attenuated energy generates less interference in the estimation of Doppler flow parameters at the second harmonic frequency. Using this path, a user may identify aliasing by viewing an image generated from the estimated Doppler parameters. Typically, the aliasing limit identified is one half of the conventional limit. In alternative embodiments, the filter 42 and parameter estimator 52 are used to estimate Doppler parameters from energy associated with fundamental frequencies.

In the second path, the Fourier transform processor 54 comprises any spectral estimator, and preferably includes fast Fourier transform estimation and auto correlation estimation. The two subsections 56, 58 are provided for separate Doppler frequency domain analysis. For example, the filter 42 is selected to pass energy associated with flow at both fundamental and harmonic frequencies. Subsection processor 56 isolates information associated with even harmonic frequencies within the Doppler domain, such as frequencies greater than negative one quarter of the pulse repetition frequency and less than one quarter of the pulse repetition frequency. The parameter estimator 60 estimates parameters at the second harmonic frequency. Subsection processor 58 isolates information associated with the fundamental frequency, such as information less than negative one quarter of the pulse repetition frequency and information greater than one quarter of the pulse repetition frequency. The parameter estimator 62 estimates parameters from the isolated information at the fundamental frequency. The subsection processors 56 and 58 and the Fourier transform processor 54 may comprise separate components or the same component, and the parameter estimators 60 and 62 may comprise one estimator. Furthermore, processing associated with the first path and the second path may be performed by the same processor. Any of the parameter estimators 52, 60, 62 estimate Doppler frequency, variance and energy parameters. Other parameters may be estimated. In alternative embodiments, the subsection processors 56 and 58 may comprise filters for isolating information in the radio frequency domain.

The estimates are passed to a processor 64 for selecting and or calculating display parameters. The processor 64 selects any of the various parameters estimated in the first and/or second paths for scan conversion and display. The processor 64 may combine various parameters or calculate further information from the estimates. For example, Doppler energy estimates at the harmonic of fundamental frequency are compared to a threshold to determine whether a Doppler velocity estimate at the harmonic or fundamental frequency is to be displayed. As another example, velocity and variance information are combined to provide one estimate for each spatial location or the Doppler frequency is converted to a Doppler velocity. The processor 64 may also scale the estimates. Velocity motion detected from harmonic energy may be selected and output, such as to identify and quantify motion with or without contrast agents. The velocity estimates of motion detecting fundamental energy may be selected and output, such as to identify blood flow containing few or no contrast agents. For example, the velocity estimates at the fundamental frequency are displayed at any spatial location where the corresponding energy at the harmonic frequency is below a threshold. Velocity estimates from fundamental frequencies may optionally be displayed with different colors. A display of energy estimates from motion detected using either harmonic or fundamental information may be displayed. The variance estimated from motion detected using harmonic information of flow may be displayed, such as to indicate the distribution of velocities or spread of velocities in an area of interest and to identify flow turbulence (e.g. turbulence behind a faulty cardiac valve).

Any of the estimates may be combined to calculate a parameter for display. For example, the energy estimate associated with flow at the second harmonic frequency is divided by the energy estimate associated with flow at the fundamental frequency for displaying a ratio parameter. The ratio may be multiplied by a constant, where the constant is determined based on the target and any optional contrast agent or other independent criteria. The ratio parameter may identify variations in contrast agent concentrations and the temporal accumulation and depletion of contrast agent in an area of interest.

The parameter selected or calculated for display is output to the scan converter 46. The scan converter 46 reformats the data from a polar coordinate system associated with the scan format to a Cartesian coordinate system associated with the display, if necessary. The scan converted information is provided to the display 48 for generation of an image. The scan converter 46 may combine the Doppler parameter(s) with B mode data to generate a display of both information at different or the same spatial locations.

The imaging techniques and systems described herein may be used for both tissue and contrast agent imaging. In contrast agent imaging, any one of a number of well known contrast agents, such as microspheres, are added to the target in order to enhance the response of tissue or fluid. Contrast agents radiate ultrasound energy at a harmonic and/or at the fundamental frequency.

In tissue imaging, no additional contrast agent is added to the target, and only the characteristics of the tissue or fluid are relied on to create the ultrasonic image. Medical ultrasound imaging is typically conducted in a discrete imaging session for a given subject at a given time. For example, an imaging session can be limited to an ultrasound patient examination of a given tissue of interest over a period of one quarter to one hour, though other durations are possible. In this case, no additional contrast agent is introduced into the tissue at any time during the imaging session. For harmonic imaging, the harmonic components are generated by processes associated with the propagation and reflection of the ultrasound signal through body tissues. For example, the carotid is imaged without the addition of contrast agents during the imaging session and the harmonic response is obtained using pulse inversion transmission and Doppler processing. Such imaging may improve motion detection since fewer acoustic reverberations and aberrations of the received harmonic signals exist as compared to received fundamental signals with equivalent spatial resolution. The reduced acoustic reverberation and aberrations may reduce the clutter component in the signal of interest, allowing for more accurate detection of motion.

In alternative embodiments, the ultrasound system includes an adaptive clutter filter. Different filters may be selected for use in different applications such as different filters for imaging of one of the carotid, kidney, liver, or heart. Adaptive filtering also includes using feedback or other information for automatically determining filter characteristics. For example, different batches of the same contrast agent or different types of contrast agents may produce varying levels of energy at even harmonic frequencies, such that both the application and the agent must be considered collectively to determine the appropriate filter characteristics. Adaptive clutter filters may improve clutter suppression, improve low velocity detection and increase the dynamic ranges of velocity estimation. These improvements may lead to more useful low velocity scale settings where the images are not corrupted by color flash and more diagnostic flow information is available to the user.

Adaptive filtering may be provided by modifying the receive signals prior to filtration and/or selection of particular filters or filter coefficients based on characteristics of the received signals. Other adaptive filtration systems may be used as discussed herein. Adaptive filtration may be used in the embodiment shown in FIG. 3, such as for adaptively selecting or modifying received signals for application to the filter 42. The adaptive filters may be adapted on a spatial location by spatial location basis. In alternative embodiments, the filter adapts on a line by line or other grouping of received signal basis.

Figure 6:
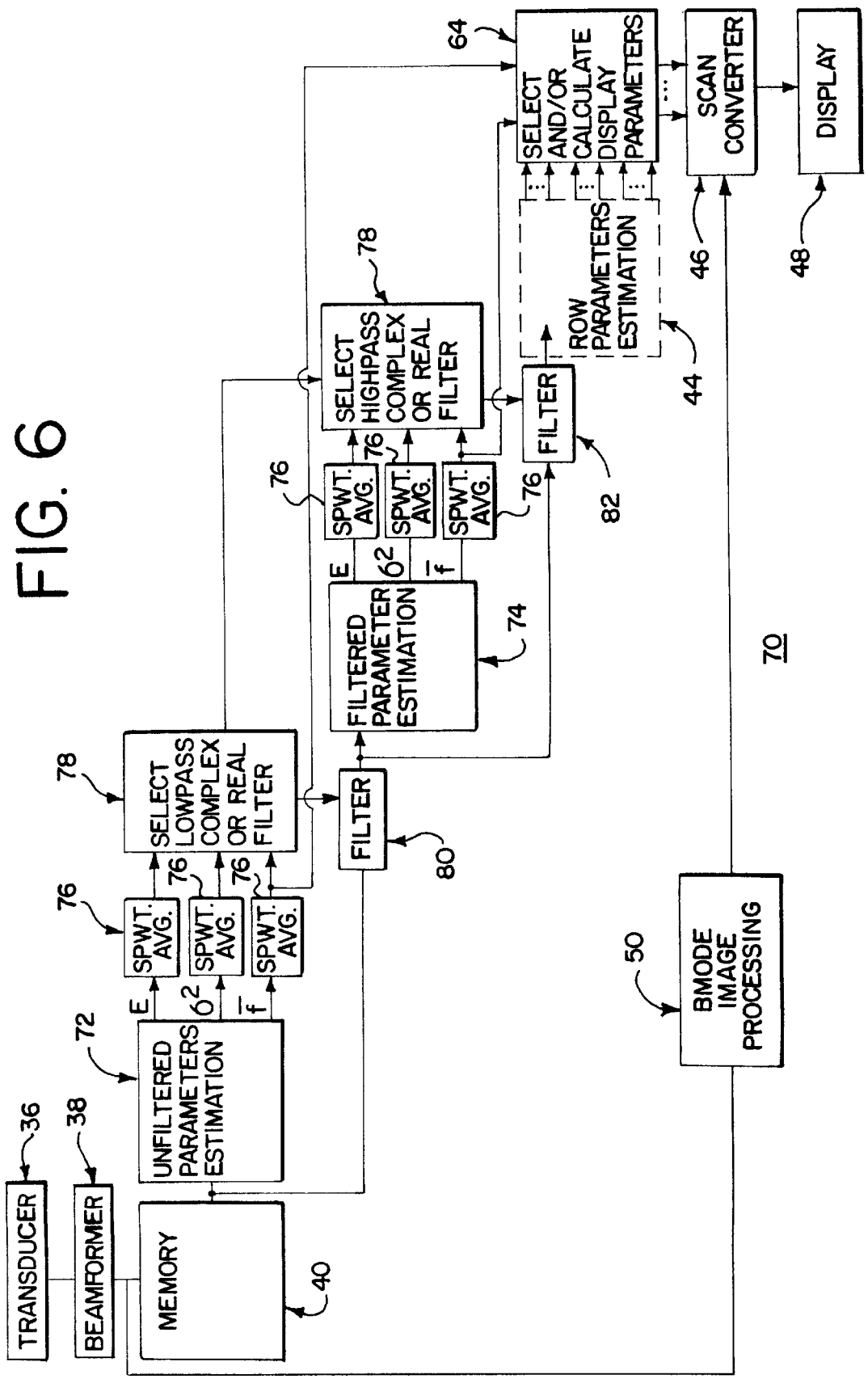
FIG. 6 is a block diagram of a first embodiment of a medical diagnostic ultrasound system for Doppler detection with an adaptive filter.

Referring to FIG. 6, a block diagram of one embodiment of a diagnostic medical ultrasound system using adaptive clutter filtering for pulse inversion transmission and Doppler motion detection is shown generally at 70. Like numerals from FIG. 3 for the same components are used for this figure and are not further detailed in the discussion of FIG. 6. The system 70 includes an adaptive filtering system with first and second parameter estimators 72 and 74, filter selectors 78 and filter components 80 and 82. The system optionally includes spatial averagers 76. For this embodiment, the first filter component 80 comprises a lowpass filter, and the second filter component 82 comprises a highpass filter. The order of filtering may be reversed or a single bandpass filter may be used. Further, a single filter with sequential lowpass and then a highpass filtering, or vice-versa, may be used. Such two pass clutter filtering systems are used to first suppress clutter at the fundamental frequency and then suppress clutter at the second harmonic frequency, or vice-versa, adaptively. The parameter estimators 72 and 74 comprise auto-correlation estimators or fast Fourier transform estimators. Other Doppler parameter estimators may be used.

The first parameter estimator 72 estimates energy, variance and/or frequency parameters. Preferably, the Doppler parameters are estimated from received signals prior to clutter filtering. In alternative embodiments, a feedback loop is used to select filter characteristics based on received signals that have been passed through the clutter filter. The estimated Doppler parameters are optionally spatially averaged by spatial averager 76. The spatial averager may comprise memory buffers and processors for spatially averaging any group of Doppler estimates.

The selection processor 78 uses one or more of the Doppler estimates to select a real or complex lowpass clutter filter component 80. The clutter filter component 80 is selected to provide the most attenuation at the same frequency as the peak clutter energy at the fundamental frequency. For example, if the peak clutter energy is at the maximum detectable Doppler frequency (i.e. PRF/2 limit), a simple lowpass real filter is selected (e.g. filter coefficients [1, 1]). In another example, an impulse filter which effectively provides no filtering is selected where the clutter associated with the fundamental response is insignificant. For example, if the energy estimate is low, no filter or a real filter may be applied, such as may be associated with imaging the center of the cartoid artery. A complex filter may be selected to position the stop band away from the maximum detectable Doppler frequency and located at or near the Doppler frequency corresponding to the estimated peak energy of the clutter at the fundamental frequency. Other lowpass filters, both FIR and IIR, may be selected.

Filters with additional coefficients may be used to vary stop band characteristics to better attenuate energy at the fundamental frequency associated with clutter. For example, the center of the stop band of the filter is selected as a function of the Doppler frequency or velocity estimate. The variance parameter is used to select the width of the stop band (e.g. high variance suggests broad clutter components and selection of a broad stop band clutter filter). The Doppler energy estimate may be used to select a filter with different attenuation levels in the filter stop band or a different stopband width. Less stopband attenuation or narrow stopband widths may improve low velocity detectability. Fewer or different estimates may be used for determining one or more of the characteristics of the filter component 80.

In one embodiment, only imaging associated with the second harmonic response is desired, so the lowpass filter is selected to significantly attenuate all energy associated with the fundamental response. For example, energy at frequencies greater than one quarter the pulse repetition frequency and energy at frequencies less than minus one quarter of the pulse repetition frequency are attenuated.

The output from the filter component 80 is provided to the other filter component 82 and the parameter estimator 74. In alternative embodiments, the received signals from before filter component 80 are provided to the parameter estimator 74. The parameter estimator 74, like the other parameter estimator 72 estimates energy, variance and/or frequency parameters. The estimates are optionally spatially averaged and used for selecting the filter characteristics of the filter component 82. In this embodiment, the filter component 82 comprises a highpass filter for removing clutter associated with the even harmonic response.

Analogous to the filter selection criteria discussed above for lowpass filtering, the Doppler estimates are used to select a highpass filter with the stop band aligned with the region associated with the strongest clutter at the second harmonic frequency. The mean Doppler frequency estimate may be used to position this stopband region, and the variance may optionally be used to select an appropriate stopband. The stopband position and width may be determined as a function of any one or more of the Doppler parameters or estimates.

In alternative embodiments, no filter or minimal attenuation is selected, allowing the data to pass unfiltered or minimally filtered. For example, the parameter estimator 74, spatial averagers 76 and selection processor 78 for use with the filter component 82 are bypassed or not provided within the system 70. Alternatively and as a function of the application and contrast agent, a real filter is adaptively selected or non-adaptively applied. This alternative embodiment may be useful when the energy associated with the flow signal at the fundamental frequency is greater than the energy associated with the clutter signal at the harmonic frequency. An energy estimate may be used to determine when no filter or a real filter is applied. For example, if the Doppler energy is low or below a threshold, the clutter associated with a harmonic response may be insignificant. Therefore, filtering is not provided or a real filter is used.

In some circumstances, the sources of clutter associated with fundamental response may be identical or similar to the sources of clutter associated with harmonic response. In these circumstances, the parameters estimated prior to passing the received signals through the first filter component 80 are used to select the second filter component 82 (i.e. the parameter estimator 74, spatial averagers 76 and/or the selection processor 78 associated with the second filter component 82 are bypassed or not provided). Inaccurate clutter estimation due to biases imposed by the first filter component 80 is avoided. The bandwidth and the associated variance of the clutter associated with the harmonic may be a scaled version of the bandwidth of the clutter associated with the fundamental. The highpass filter response is selected to have a stopband width that is a scaled version of the lowpass filter response stopband width.

Experimentation with various contrast agents and imaging applications of interest may be used to determine the optimal filters. In alternative embodiments one or more Doppler estimates from one stage within the system 70 are used in combination with one or more Doppler estimates used from another stage of the system 70 for selection of a filter or filter characteristic.

Figure 8:
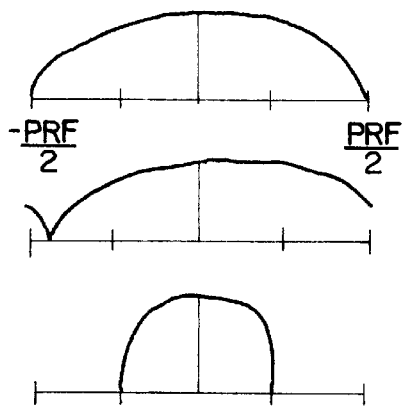
FIG. 8 is a graphical representation of lowpass filter responses of an adaptive filter.
Figure 9:
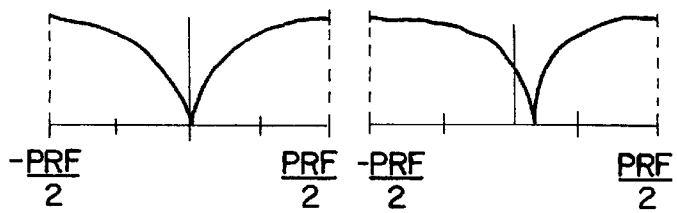
FIG. 9 is a graphical representation of highpass filter responses of an adaptive filter.

After the received signals are passed through a lowpass filter response of the filter component 80 and the highpass filter response of the filter component 82, Doppler parameters are estimated as discussed above with regard to FIG. 3 by the Doppler processor 44. The Doppler parameters for display are then selected by the processor 64. FIG. 8 represents various lowpass frequency responses for selection of the filter component 80. As shown, wide bandwidth and narrow bandwidth real lowpass filter responses are shown. Also shown is a complex lowpass filter response where the null is not symmetrical about the zero frequency. FIG. 9 shows various highpass frequency responses for selection in implementing the filter component 82. Real highpass filter and complex highpass filter responses are demonstrated.

In the system 70, the processor 64 preferably includes inputs for the additional Doppler frequency estimates from the previous stages. In alternative embodiments, no additional frequency estimates are provided from previous stages or other parameters from the previous stages may also be provided as inputs to the processor 64. These additional Doppler frequency estimates are preferably used so that the final frequency and corresponding velocity estimates are referenced to the clutter. For example, if the velocity of flow associated with the harmonic response is equal to a constant, k, multiplied by the pulse repetition frequency divided by four with respect to the transducer as a reference, and the frequency associated with the clutter of the harmonic response is equal to the pulse repetition frequency divided by 16, the velocity of the flow of the harmonic response is altered to be referenced to the clutter (i.e., k(PRF/4-PRF/16). The frequency inputs from the previous stage are used to identify the frequency associated with the clutter at the fundamental and/or harmonic frequencies.

In alternative embodiments, feedback loops are implemented so that fewer parameters estimators, selection processors and/or filter components are provided. The data is sequentially processed and stored in a memory for subsequent processing through the same loop for each of lowpass filtering, highpass filtering and/or final parameter estimation.

Figure 7:
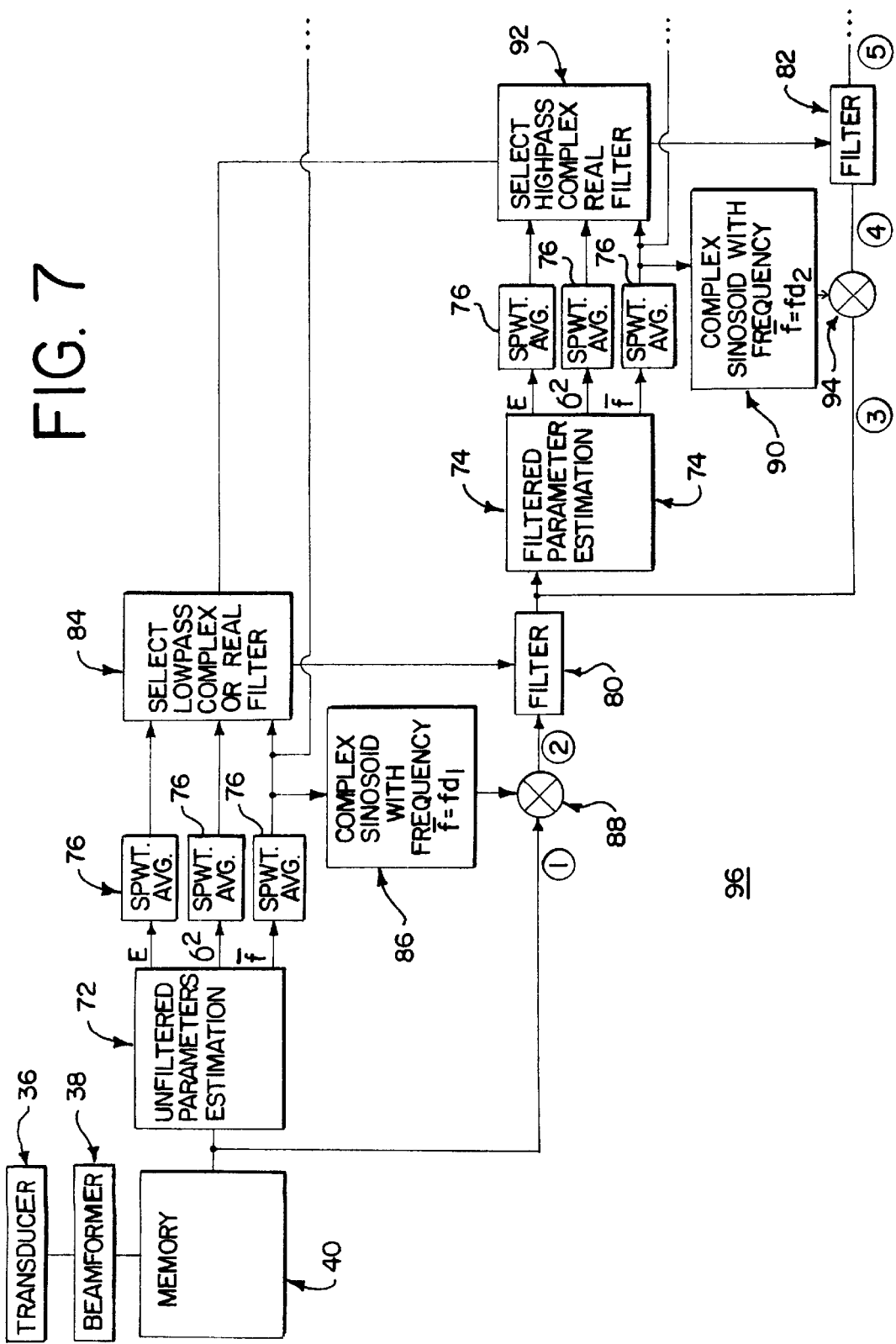
FIG. 7 is a block diagram of a second embodiment of a medical ultrasound diagnostic system for Doppler detection with an adaptive filter.

Referring to FIG. 7, another preferred embodiment of a system for implementing adaptive clutter filtering is shown at 96. In this embodiment, the received signals are altered to move the peak energy associated with one or both of the fundamental and harmonic response of clutter to a position appropriate for attenuation by a real filter. The system 96 includes two filtering stages. In the first filtering stage, the parameter estimator 72 and optional spatial averagers 76 provide Doppler parameter estimates to the selection processor 84.

The Doppler frequency estimate is also provided to a processor 86 for determining a complex sinusoid. The processor 86 generates a complex sinusoid with quadrature phase components of the mean frequency sampled at the same rate as the sampled signals from parameter estimator 72 and optional spatial averagers 76. The complex sinusoid may be mathematically represented as $e^{j2\pi f_{di} t}$, where t is the sampling time and $f_{di}$ is the Doppler frequency shift. The Doppler frequency shift is equal to $2if_0 V_{fi}/c$, where $f_0$ is the fundamental frequency, i is an integer corresponding to the harmonic, (i.e. i=2 for the second harmonic and i=1 for the fundamental), and c is the speed of sound. The processor 86 may alternatively, partly or wholly, consist of a programmable or fixed read only memory unit (ROM).

The complex sinusoid is multiplied with the receive signals by multiplier 88. The modulated information is provided to the filter component 80. As discussed above, the frequency response of the filter component 80 is preferably selected to be a lowpass real filter by the selection processor 84.

Figure 10:
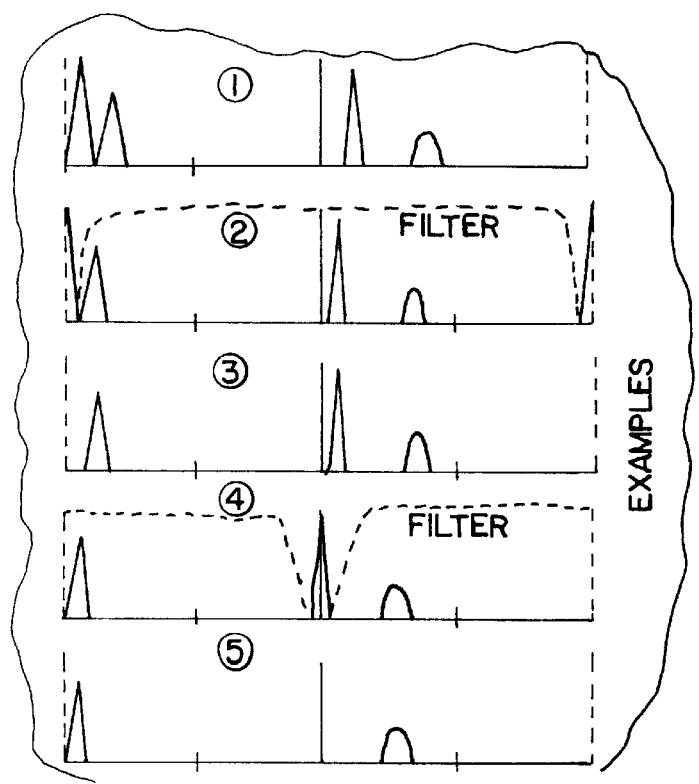
FIG. 10 is a graphical representation of Doppler spectra at various points within the medical diagnostic ultrasound system of FIG. 7.

Referring to FIG. 10, a graphical representation of the frequency response of signals at various locations in the system 96 of FIG. 7 are shown. Prior to the multiplier 88, the Doppler domain spectra includes clutter and flow energy at fundamental and harmonic frequencies. Multiplier 88 uses the complex sinusoid as a reference signal to shift the mean frequency of the clutter signal at the fundamental frequency to one half the pulse repetition frequency. The output of the multiplier 88 at location 2 is shown in FIG. 10. Based on one or more of the estimated parameters, a real filter is selected for implementation by the filter component 80. Preferably, the real filter comprises a lowpass filter for attenuating the energy associated with clutter at the fundamental frequency. The filtered information at the third location is shown in FIG. 10 and is passed to the next stage for attenuation of clutter associated with the harmonic response.

The process is repeated in the next stage for highpass filtering. Using a real highpass filter allows attenuation of clutter at the second harmonic. The highpass filtering stage may be placed prior to the lowpass filtering stage, or a single bandpass filtering stage may be used. The parameter estimator 74 and optional spatial averager 76 are used to generate Doppler parameters, such as energy, variance and/or frequency for selection of the highpass filter response. The Doppler frequency estimate is passed to a processor 90 for generation of an additional complex sinusoid. In alternative embodiments, a loop structure is used so that the same processors may be used in each stage or the same estimates are used for selection of the highpass filter as were used for selection of the lowpass filter.

Using the mean frequency associated with the clutter at the harmonic frequency, the processor 90 generates a complex sinusoid for shifting the peak energy associated with the harmonic clutter to the zero frequency. By multiplying the complex sinusoid with the output of the filter component 80, the multiplier 94 generates the spectra at location 4 as shown in FIG. 10. A real highpass filter is selected as discussed above for implementation by the filter component 82. The highpass filter is preferably a real filter selected to attenuate the energy associated with clutter at the harmonic response. The output of the filter component 82 provides the spectral response at location 5 as shown in FIG. 10. This spectral response includes flow associated with the harmonic response and flow associated with the fundamental response where the clutter of both the fundamental and harmonic components has been attenuated.

In alternative embodiments, the real filter impulse response is modulated to generate a complex filter. The output of the filter component 82, and, optionally, the output of various parameters estimated by the other parameter estimators 72 and 74 are provided to the Doppler processor 44 as discussed above with respect to FIGS. 3 and 6 for subsequent generation of a image.

In alternative embodiments of adaptive filtering, a bandpass adaptive clutter filter is provided. Improved harmonic Doppler motion detection is implemented by replacing the highpass filtering stages of FIG. 6 or 7 with a fast Fourier transform estimator. In one embodiment, the fast Fourier transform estimator comprises the second path for estimation of Doppler parameters as shown in FIG. 3 (e.g., FFT 54, subsection processor 56 and/or 58 and parameter estimation processor 60 and/or 62). A fast Fourier transform is performed, and information associated with the second harmonic and fundamental is isolated by the subsection blocks. Doppler parameters are estimated from the information. Parameters may be further estimated, such as by the Doppler processor 44 after the highpass filtering stage in FIG. 6, and an output selected by the processor 64. In other alternative embodiments, combinations of selection of complex filter responses, modulation of the data prior to filtering, and modulation of real filters may be used.

In an alternate embodiment, B-mode processing is used as a substitute for the Doppler processing discussed above. Data obtained from filtering signals associated with pulse inversion techniques is provided to a B-mode processor. B-mode processing, whether the results are displayed in color or black and white, provides information similar to Doppler energy processing.

As used herein, the term harmonic is intended to broadly encompass subharmonics and integer harmonics (e.g. second, third, fourth or other integer harmonic) as well as fractional harmonics (e.g. 3/2, 5/2 or others).

While the invention has been described above by reference to various embodiments, it will be understood that many changes and modifications can be made without departing from the scope of the invention. For example, different scan line geometries, including sector, Vector®, and parallel beam geometries may be used. Various bandpass, highpass, or lowpass filter responses may be used. Any filter component may be adaptive or non-adaptive. For adaptive filtering, the criteria used for selecting the filter may be provided from any of various sources.

It is therefore intended that the foregoing detailed description be understood as an illustration of the presently preferred embodiments of the invention and not as a definition of the invention. It is only the following claims, including all equivalents, that are intended to define the scope of this invention.

What is claimed is:

1. A method for detecting information using Doppler processing with a medical diagnostic ultrasound system, the method comprising the steps of:
   (a) transmitting a first ultrasonic pulse of a first polarity;
   (b) transmitting a second ultrasonic pulse of a second polarity;
   (c) clutter filtering receive signals responsive to steps (a) and (b) with a lowpass filter comprising at least three taps; and
   (d) Doppler processing the filtered receive signals.

2. The method of claim 1 wherein:
   steps (a) and (b) comprise transmitting along a same scan line; and
   step (c) comprises filtering receive signals associated with the same depths along the scan line.

3. The method of claim 2 wherein steps (a) and (b) comprise transmitting pulses which differ by a phase of respective envelopes.

4. The method of claim 1 wherein step (c) comprises suppressing clutter signals associated with a fundamental transmit frequency.

5. The method of claim 1 wherein step (c) comprises filtering the receive signals with a bandpass filter.

6. The method of claim 5 wherein step (c) comprises suppressing clutter signals associated with a fundamental transmit frequency and a harmonic of the fundamental transmit frequency.

7. The method of claim 5 wherein step (c) comprises filtering the receive signals with the lowpass filter and a highpass filter; and
   wherein step (d) comprises Doppler processing the filtered receive signals.

8. The method of claim 5 further comprising:
   (e) outputting Doppler estimates at a fundamental transmit frequency.

9. The method of claim 5 further comprising:
   (e) outputting Doppler estimates at a harmonic frequency of a fundamental transmit frequency.

10. The method of claim 5 further comprising:
    (e) outputting Doppler energy estimates comprising a ratio of Doppler energy estimates at a fundamental transmit frequency and Doppler energy estimates at a harmonic frequency of the fundamental transmit frequency.

11. The method of claim 1 wherein steps (a) and (b) comprise transmitting into a target during an imaging session, the target being free of contrast agent through the entire imaging session.

12. The method of claim 1 further comprising:
    (e) outputting Doppler estimates at a harmonic frequency of a fundamental transmit frequency.

13. The method of claim 1 wherein step (c) comprises filtering with an adaptive filter.

14. The method of claim 13 further comprising:
    (e) multiplying the received signals with a complex sinusoid.

15. The method of claim 14 wherein step (c) comprises filtering the multiplied received signals of step (e) with a real lowpass filter.

16. The method of claim 14 further comprising:
    (f) determining a Doppler frequency from the receive signals; and
    (g) generating the complex sinusoid as a function of the Doppler frequency.

17. The method of claim 16 wherein the Doppler frequency comprises fundamental information; and further comprising:
    (h) determining a Doppler frequency of harmonic information;
    (i) generating another complex sinusoid as a function of the Doppler frequency of the harmonic information;
    (j) multiplying the output of step (e) with the other complex sinusoid; and
    (k) filtering the output of step (j) with a real highpass filter.

18. The method of claim 13 further comprising:
    (e) selecting the lowpass filter as a function of at least one Doppler estimate.

19. The method of claim 18 wherein step (c) comprises filtering with the selected lowpass filter, the lowpass filter comprising a complex filter.

20. The method of claim 18 further comprising:
    (f) selecting a highpass filter as a function of an estimate selected from the group consisting of: at least one Doppler estimate, at least one Doppler estimate from the output of the lowpass filter, and combinations thereof;

(g) filtering the output of the lowpass filter with the selected highpass filter, the highpass filter comprising a complex filter.

21. The method of claim 18 wherein step (c) comprises filtering the multiplied received signals of step (e) with a bandpass filter.

22. The method of claim 1 further comprising (e) transmitting at least a third ultrasonic pulse wherein step (c) comprises filtering receive signals responsive to at least the first, second and third ultrasonic pulses.

23. A medical diagnostic ultrasound system for detecting information using Doppler processing, the system comprising:
   a transducer;
   a beamformer operatively connected to the transducer for transmitting first and second ultrasonic pulses of first and second respective polarities at a fundamental frequency;
   a lowpass clutter filter operatively connected to the transducer and comprising at least three taps for filtering receive signals responsive to the first and second ultrasonic pulses; and
   a Doppler processor operatively connected to the lowpass filter for generating estimates.

24. The system of claim 23 wherein the lowpass filter comprises a bandpass filter.

25. The system of claim 24 wherein the bandpass filter comprises the lowpass filter and a highpass filter; and
   wherein the Doppler processor is operatively connected to the output of the bandpass filter.

26. The system of claim 23 wherein the lowpass filter comprises an adaptive filter.

27. The system of claim 26 further comprising:
   a multiplier operable to modulate the received signals with a complex sinusoid.

28. The system of claim 27 further comprising:
   a second Doppler processor operable to determine a Doppler frequency from the receive signals; and
   a means for generating the complex sinusoid as a function of the Doppler frequency.

29. The system of claim 28 wherein the Doppler frequency comprises fundamental information; and further comprising:
   a third Doppler processor operable to determine a Doppler frequency of harmonic information;
   a second means for generating another complex sinusoid as a function of the Doppler frequency of the harmonic information;
   a second multiplier operable to multiply the output of the lowpass filter with the other complex sinusoid; and
   a real highpass filter operatively connected to the second multiplier.

30. The system of claim 26 further comprising a second Doppler processor operable to estimate a Doppler parameter;
   wherein the lowpass filter is selectable as a function of at least the estimate of the Doppler parameter.

31. The system of claim 30 wherein the lowpass filter comprises a complex filter.

32. The system of claim 30 further comprising:
   a selectable highpass filter operable to filter the output of the lowpass filter, the selectable highpass filter selected as a function of an estimate selected from the group consisting of: the estimate of the Doppler parameter, a Doppler estimate from the output of the lowpass filter, and combinations thereof.

33. The system of claim 23 wherein the beamformer is operative to transmit at least a third ultrasonic pulse and the lowpass filter is operative to filter receive signals responsive to at least the first, second and third ultrasonic pulses.

34. A method for detecting information using Doppler processing with a medical diagnostic ultrasound system, the method comprising the steps of:
   (a) transmitting a first ultrasonic pulse of a first polarity;
   (b) transmitting a second ultrasonic pulse of a second polarity;
   (c) clutter filtering receive signals responsive to steps (a) and (b) with a lowpass filter comprising at least two taps, the at least two taps responsive to different weights; and
   (d) Doppler processing the filtered receive signals.

35. The method of claim 34 wherein:
   steps (a) and (b) comprise transmitting along a same scan line; and
   step (c) comprises filtering receive signals associated with the same depths along the scan line.

36. The method of claim 35 wherein steps (a) and (b) comprise transmitting pulses which differ by a phase of respective envelopes.

37. The method of claim 34 wherein step (c) comprises suppressing clutter signals associated with a fundamental transmit frequency.

38. The method of claim 34 wherein step (c) comprises filtering the receive signals with a bandpass filter.

39. The method of claim 38 wherein step (c) comprises suppressing clutter signals associated with a fundamental transmit frequency and a harmonic of the fundamental transmit frequency.

40. The method of claim 38 wherein step (c) comprises filtering the receive signals with the lowpass filter and a highpass filter; and
   wherein step (d) comprises Doppler processing the filtered receive signals.

41. The method of claim 38 further comprising:
   (e) outputting Doppler estimates at a fundamental transmit frequency.

42. The method of claim 38 further comprising:
   (e) outputting Doppler estimates at a harmonic frequency of a fundamental transmit frequency.

43. The method of claim 38 further comprising:
   (e) outputting Doppler energy estimates comprising a ratio of Doppler energy estimates at a fundamental transmit frequency and Doppler energy estimates at a harmonic frequency of the fundamental transmit frequency.

44. The method of claim 34 wherein steps (a) and (b) comprise transmitting into a target during an imaging session, the target being free of contrast agent through the entire imaging session.

45. The method of claim 34 further comprising:
   (e) outputting Doppler estimates at a harmonic frequency of a fundamental transmit frequency.

46. The method of claim 34 wherein step (c) comprises filtering with an adaptive filter.

47. The method of claim 46 further comprising:
   (e) multiplying the received signals with a complex sinusoid.

48. The method of claim 47 wherein step (c) comprises filtering the multiplied received signals of step (e) with a real lowpass filter.

49. The method of claim 47 further comprising:
(f) determining a Doppler frequency from the receive signals; and
(g) generating the complex sinusoid as a function of the Doppler frequency.

50. The method of claim 49 wherein the Doppler frequency comprises fundamental information; and further comprising:
(h) determining a Doppler frequency of harmonic information;
(i) generating another complex sinusoid as a function of the Doppler frequency of the harmonic information,
(j) multiplying the output of step (e) with the other complex sinusoid; and
(k) filtering the output of step (j) with a real highpass filter.

51. The method of claim 46 further comprising:
(e) selecting the lowpass filter as a function of at least one Doppler estimate.

52. The method of claim 51 wherein step (c) comprises filtering with the selected lowpass filter, the lowpass filter comprising a complex filter.

53. The method of claim 51 further comprising:
(f) selecting a highpass filter as a function of an estimate selected from the group consisting of: at least one Doppler estimate, at least one Doppler estimate from the output of the lowpass filter, and combinations thereof;
(g) filtering the output of the lowpass filter with the selected highpass filter, the highpass filter comprising a complex filter.

54. The method of claim 51 wherein step (c) comprises filtering the multiplied received signals of step (e) with a bandpass filter.

55. The method of claim 34 further comprising (e) transmitting at least a third ultrasonic pulse wherein steps (c) comprises filtering receive signals responsive to at least the first, second and third ultrasonic pulses.

56. A medical diagnostic ultrasound system for detecting information using Doppler processing, the system comprising:
a transducer;
a beamformer operatively connected to the transducer for transmitting first and second ultrasonic pulses of first and second respective polarities at a fundamental frequency;
a lowpass clutter filter operatively connected to the transducer and comprising at least two taps for filtering receive signals responsive to the first and second ultrasonic pulses, two of said at least two taps responsive to different weights; and
a Doppler processor operatively connected to the lowpass filter for generating estimates.

57. The system of claim 56 wherein the lowpass filter comprises a bandpass filter.

58. The system of claim 57 wherein the bandpass filter comprises the lowpass filter and a highpass filter; and
wherein the Doppler processor is operatively connected to the output of the bandpass filter.

59. The system of claim 56 wherein the lowpass filter comprises an adaptive filter.

60. The system of claim 59 further comprising:
a multiplier operable to modulate the received signals with a complex sinusoid.

61. The system of claim 60 further comprising:
a second Doppler processor operable to determine a Doppler frequency from the receive signals; and
a means for generating the complex sinusoid as a function of the Doppler frequency.

62. The system of claim 61 wherein the Doppler frequency comprises fundamental information; and further comprising:
a third Doppler processor operable to determine a Doppler frequency of harmonic information;
a second means for generating another complex sinusoid as a function of the Doppler frequency of the harmonic information;
a second multiplier operable to multiply the output of the lowpass filter with the other complex sinusoid; and
a real highpass filter operatively connected to the second multiplier.

63. The system of claim 59 further comprising a second Doppler processor operable to estimate a Doppler parameter;
wherein the lowpass filter is selectable as a function of at least the estimate of the Doppler parameter.

64. The system of claim 63 wherein the lowpass filter comprises a complex filter.

65. The system of claim 63 further comprising:
a selectable highpass filter operable to filter the output of the lowpass filter, the selectable highpass filter selected as a function of an estimate selected from the group consisting of: the estimate of the Doppler parameter, a Doppler estimate from the output of the lowpass filter, and combinations thereof.

66. The system of claim 56 wherein the beamformer is operative to transmit at least a third ultrasonic pulse and the lowpass filter is operative to filter receive signals responsive to at least the first, second and third ultrasonic pulses.

67. A method for detecting information using Doppler processing with a medical diagnostic ultrasound system, the method comprising the steps of:
(a) transmitting a first ultrasonic pulse of a first polarity;
(b) transmitting a second ultrasonic pulse of a second polarity;
(c) clutter filtering receive signals responsive to steps (a) and (b) with an infinite impulse response lowpass filter; and
(d) Doppler processing the filtered receive signals.

68. The method of claim 67 wherein:
steps (a) and (b) comprise transmitting along a same scan line; and
step (c) comprises filtering receive signals associated with the same depths along the scan line.

69. The method of claim 68 wherein steps (a) and (b) comprise transmitting pulses which differ by a phase of respective envelopes.

70. The method of claim 67 wherein step (c) comprises suppressing clutter signals associated with a fundamental transmit frequency.

71. The method of claim 67 wherein step (c) comprises filtering the receive signals with a bandpass filter.

72. The method of claim 71 wherein step (c) comprises suppressing clutter signals associated with a fundamental transmit frequency and a harmonic of the fundamental transmit frequency.

73. The method of claim 71 wherein step (c) comprises filtering the receive signals with the lowpass filter and a highpass filter; and wherein step (d) comprises Doppler processing the filtered receive signals.

74. The method of claim 71 further comprising:
(e) outputting Doppler estimates at a fundamental transmit frequency.

75. The method of claim 71 further comprising:
(e) outputting Doppler estimates at a harmonic frequency of a fundamental transmit frequency.

76. The method of claim 71 further comprising:
(e) outputting Doppler energy estimates comprising a ratio of Doppler energy estimates at a fundamental transmit frequency and Doppler energy estimates at a harmonic frequency of the fundamental transmit frequency.

77. The method of claim 67 wherein steps (a) and (b) comprise transmitting into a target during an imaging session, the target being free of contrast agent through the entire imaging session.

78. The method of claim 67 further comprising:
(e) outputting Doppler estimates at a harmonic frequency of a fundamental transmit frequency.

79. The method of claim 67 wherein step (c) comprises filtering with an adaptive filter.

80. The method of claim 79 further comprising:
(e) multiplying the received signals with a complex sinusoid.

81. The method of claim 80 wherein step (c) comprises filtering the multiplied received signals of step (e) with a real lowpass filter.

82. The method of claim 80 further comprising:
(f) determining a Doppler frequency from the receive signals; and
(g) generating the complex sinusoid as a function of the Doppler frequency.

83. The method of claim 80 wherein the Doppler frequency comprises fundamental information; and further comprising:
(h) determining a Doppler frequency of harmonic information;
(i) generating another complex sinusoid as a function of the Doppler frequency of the harmonic information,
(j) multiplying the output of step (e) with the other complex sinusoid; and
(k) filtering the output of step (j) with a real highpass filter.

84. The method of claim 79 further comprising:
(e) selecting the lowpass filter as a function of at least one Doppler estimate.

85. The method of claim 84 wherein step (c) comprises filtering with the selected lowpass filter, the lowpass filter comprising a complex filter.

86. The method of claim 84 further comprising:
(f) selecting a highpass filter as a function of an estimate selected from the group consisting of: at least one Doppler estimate, at least one Doppler estimate from the output of the lowpass filter, and combinations thereof;
(g) filtering the output of the lowpass filter with the selected highpass filter, the highpass filter comprising a complex filter.

87. The method of claim 84 wherein step (c) comprises filtering the multiplied received signals of step (e) with a bandpass filter.

88. The method of claim 67 further comprising (e) transmitting at least a third ultrasonic pulse wherein step (c) comprises filtering receive signals responsive to at least the first, second and third ultrasonic pulses.

89. A medical diagnostic ultrasound system for detecting information using Doppler processing, the system comprising:
a transducer;
a beamformer operatively connected to the transducer for transmitting first and second ultrasonic pulses of first and second respective polarities at a fundamental frequency;
an infinite impulse response lowpass clutter filter operatively connected to the transducer for filtering receive signals responsive to the first and second ultrasonic pulses; and
a Doppler processor operatively connected to the lowpass filter for generating estimates.

90. The system of claim 89 wherein the lowpass filter comprises a bandpass filter.

91. The system of claim 90 wherein the bandpass filter comprises the lowpass filter and a highpass filter; and
wherein the Doppler processor is operatively connected to the output of the bandpass filter.

92. The system of claim 89 wherein the lowpass filter comprises an adaptive filter.

93. The system of claim 92 further comprising:
a multiplier operable to modulate the received signals with a complex sinusoid.

94. The system of claim 93 further comprising:
a second Doppler processor operable to determine a Doppler frequency from the receive signals; and
a means for generating the complex sinusoid as a function of the Doppler frequency.

95. The system of claim 94 wherein the Doppler frequency comprises fundamental information; and further comprising:
a third Doppler processor operable to determine a Doppler frequency of harmonic information;
a second means for generating another complex sinusoid as a function of the Doppler frequency of the harmonic information;
a second multiplier operable to multiply the output of the lowpass filter with the other complex sinusoid; and
a real highpass filter operatively connected to the second multiplier.

96. The system of claim 92 further comprising a second Doppler processor operable to estimate a Doppler parameter;
wherein the lowpass filter is selectable as a function of at least the estimate of the Doppler parameter.

97. The system of claim 96 wherein the low pass filter comprises a complex filter.

98. The system of claim 96 further comprising:
a selectable highpass filter operable to filter the output of the lowpass filter, the selectable highpass filter selected as a function of an estimate selected from the group consisting of: the estimate of the Doppler parameter, a Doppler estimate from the output of the lowpass filter, and combinations thereof.

99. The system of claim 89 wherein the beamformer is operative to transmit at least a third ultrasonic pulse and the lowpass filter is operative to filter receive signals responsive to at least the first, second and third ultrasonic pulses.

100. A method for detecting information using Doppler processing from a target with a medical diagnostic ultrasound system, the method comprising the steps of:
(a) transmitting a first ultrasonic pulse of a first polarity into the target along a scan line during an imaging session, the target being free of contrast agent throughout the entire imaging session;

(b) transmitting a second ultrasonic pulse of a second polarity into the target along the scan line during the imaging session;

(c) filtering receive signals responsive to steps (a) and (b) associated with the same depths along the scan line; and (d) Doppler processing the filtered receive signals.

101. The method of claim 100 wherein step (c) comprises filtering the receive signals with a highpass filter.

102. The method of claim 101 wherein step (c) comprises suppressing clutter information at a harmonic of a fundamental transmit frequency.

103. The method of claim 100 wherein step (c) comprises filtering the receive signals with a lowpass filter.

104. The method of claim 103 wherein step (c) comprises suppressing clutter signals associated with a fundamental transmit frequency.

105. The method of claim 100 wherein step (c) comprises filtering the receive signals with a bandpass filter.

106. The method of claim 105 wherein step (c) comprises suppressing clutter signals associated with a fundamental transmit frequency and a harmonic of the fundamental transmit frequency.

107. The method of claim 105 wherein step (c) comprises filtering the receive signals with a lowpass filter and a highpass filter; and wherein step (d) comprises Doppler processing the filtered receive signals.

108. The method of claim 107 wherein filtering with the highpass filter comprises suppressing clutter signals associated with a harmonic of a fundamental transmit frequency.

109. The method of claim 105 further comprising:

(e) outputting Doppler estimates at a fundamental transmit frequency.

110. The method of claim 105 further comprising:

(e) outputting Doppler estimates at a harmonic frequency of a fundamental transmit frequency.

111. The method of claim 105 further comprising:

(e) outputting Doppler energy estimates comprising a ratio of Doppler energy estimates at a fundamental transmit frequency and Doppler energy estimates at a harmonic frequency of the fundamental transmit frequency.

112. The method of claim 105 wherein step (d) comprises outputting Doppler estimates comprising a combination of Doppler estimates at a fundamental frequency and Doppler estimates at a harmonic frequency of the fundamental frequency.

113. The method of claim 100 wherein steps (a), (b), (c) and (d) are repeated for a plurality of scan lines.

114. The method of claim 100 further comprising:

(e) transmitting at least a third ultrasonic pulse;

wherein step (c) comprises filtering receive signals responsive to at least the first, second and third ultrasonic pulses.

115. The method of claim 100 further comprising:

(e) outputting Doppler estimates at a harmonic frequency of a fundamental transmit frequency.

116. The method of claim 100 wherein step (c) comprises filtering with an adaptive clutter filter.

117. The method of claim 116 further comprising:

(e) multiplying the received signals with a complex sinusoid.

118. The method of claim 117 further comprising:

(f) determining a Doppler frequency from the receive signals; and (g) generating the complex sinusoid as a function of the Doppler frequency.

119. The method of claim 116 further comprising:

(e) selecting the adaptive clutter filter as a function of a Doppler estimate, the adaptive clutter filter comprising a complex filter.

120. The method of claim 100 wherein steps (a) and (b) comprise transmitting pulses which differ by a phase of respective envelopes.

121. A method for detecting information using Doppler processing with a medical diagnostic ultrasound system, the method comprising:

(a) obtaining signals responsive to different transmitted polarities; and (b) removing clutter in said signals associated with harmonic frequencies.

122. The method of claim 121 wherein (b) comprises filtering with a filter having at least three taps.

123. The method of claim 121 wherein (b) comprises filtering with an IIR filter.

124. The method of claim 121 wherein (b) comprises filtering with a filter having at least two taps with filtering coefficients comprising different weights.

125. The method of claim 121 wherein (b) comprises filtering operative to removing clutter in the signals associated with fundamental frequencies.

* * * * *